US010441349B2

(12) United States Patent
Sartor et al.

(10) Patent No.: US 10,441,349 B2
(45) Date of Patent: *Oct. 15, 2019

(54) NON-STICK COATED ELECTROSURGICAL INSTRUMENTS AND METHOD FOR MANUFACTURING THE SAME

(71) Applicant: COVIDIEN LP, Mansfield, MA (US)

(72) Inventors: Joe D. Sartor, Longmont, CO (US); William E. Robinson, Boulder, CO (US); Todd W. Boucher, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 252 days.

This patent is subject to a terminal disclaimer.

(21) Appl. No.: 15/332,797

(22) Filed: Oct. 24, 2016

(65) Prior Publication Data
US 2017/0119456 A1 May 4, 2017

Related U.S. Application Data

(63) Continuation-in-part of application No. 14/926,553, filed on Oct. 29, 2015.

(51) Int. Cl.
*A61B 18/14* (2006.01)
*A61B 18/16* (2006.01)
(Continued)

(52) U.S. Cl.
CPC ...... *A61B 18/1442* (2013.01); *A61B 18/1445* (2013.01); *A61B 2018/0013* (2013.01);
(Continued)

(58) Field of Classification Search
CPC ............ A61B 18/1442; A61B 18/1445; A61B 2018/00083; A61B 2018/00107;
(Continued)

(56) References Cited

U.S. PATENT DOCUMENTS 3,729,007 A  4/1973 Mirkovitch
4,100,113 A  7/1978 McCain
(Continued)

FOREIGN PATENT DOCUMENTS

CN  1649887 A  8/2005
EP  0 331 774 A1  9/1989
(Continued)

OTHER PUBLICATIONS

Extended European Search Report corresponding to European Application No. 09755793.8, dated Jul. 21, 2014; 8 pages.
(Continued)

*Primary Examiner* — Michael F Peffley

(57) ABSTRACT

An end effector assembly for use with an electrosurgical instrument is provided. The electrosurgical instrument includes a handle having a shaft that extends therefrom, an end effector disposed at a distal end of the shaft, at least one electrode operably coupled to the end effector and adapted to couple to a source of electrosurgical energy, a titanium nitride coating covering at least a portion of the electrode, a chromium nitride coating covering at least a portion of the electrode and/or titanium nitride coating, and a hexamethyldisiloxane plasma coating covering at least a portion of the chromium nitride coating.

17 Claims, 12 Drawing Sheets

(51) Int. Cl.
*A61B 18/00* (2006.01)
*A61B 34/20* (2016.01)

(52) U.S. Cl.
CPC .............. *A61B 2018/0063* (2013.01); *A61B 2018/00083* (2013.01); *A61B 2018/00107* (2013.01); *A61B 2018/00136* (2013.01); *A61B 2018/00148* (2013.01); *A61B 2018/162* (2013.01); *A61B 2034/2059* (2016.02); *A61B 2034/2061* (2016.02); *A61B 2034/2065* (2016.02)

(58) Field of Classification Search
CPC .. A61B 2018/0013; A61B 2018/00136; A61B 2018/00148; A61B 2018/0063; A61B 2018/162
See application file for complete search history.

(56) References Cited

U.S. PATENT DOCUMENTS

| | | | |
|---|---|---|---|
| 4,348,426 A | 9/1982 | Blenner et al. | |
| 4,396,450 A | 8/1983 | Blenner et al. | |
| 4,492,231 A | 1/1985 | Auth | |
| 4,714,650 A | 12/1987 | Obayashi et al. | |
| 5,201,900 A | 4/1993 | Nardella | |
| 5,211,993 A | 5/1993 | Kolesinski | |
| 5,484,436 A | 1/1996 | Eggers et al. | |
| 5,549,604 A | 8/1996 | Sutcu et al. | |
| 5,702,387 A | 12/1997 | Arts et al. | |
| 5,713,895 A | 2/1998 | Lontine et al. | |
| 5,773,098 A | 6/1998 | Thomas | |
| 5,925,043 A | 7/1999 | Kumar et al. | |
| 5,965,629 A | 10/1999 | Jung et al. | |
| 6,066,137 A | 5/2000 | Greep | |
| 6,070,444 A | 6/2000 | Lontine et al. | |
| 6,139,547 A | 10/2000 | Lontine et al. | |
| 6,146,462 A | 11/2000 | Yializis et al. | |
| 6,159,531 A | 12/2000 | Dang et al. | |
| 6,293,946 B1 | 9/2001 | Thorne | |
| 6,300,641 B1 | 10/2001 | Koh et al. | |
| 6,408,755 B1 | 6/2002 | Meisters et al. | |
| 6,428,861 B2 | 8/2002 | France et al. | |
| 6,485,961 B1* | 11/2002 | Meserol | A61N 1/0412 204/290.12 |
| 6,486,135 B1 | 11/2002 | Li et al. | |
| 6,534,133 B1 | 3/2003 | Kaloyeros et al. | |
| 6,548,121 B1 | 4/2003 | Bauer et al. | |
| 6,582,429 B2 | 6/2003 | Krishnan et al. | |
| 6,602,552 B1 | 8/2003 | Daraskevich et al. | |
| 6,730,275 B2 | 5/2004 | Sharma et al. | |
| 6,774,018 B2 | 8/2004 | Mikhael et al. | |
| 6,869,676 B2 | 3/2005 | Burger et al. | |
| 6,932,816 B2 | 8/2005 | Phan | |
| 6,951,559 B1 | 10/2005 | Greep | |
| 6,953,461 B2 | 10/2005 | McClurken et al. | |
| 7,067,405 B2 | 6/2006 | Mikhael et al. | |
| 7,083,618 B2 | 8/2006 | Couture et al. | |
| 7,147,634 B2 | 12/2006 | Nesbitt | |
| 7,156,842 B2 | 1/2007 | Sartor et al. | |
| 7,214,413 B2 | 5/2007 | Koulik et al. | |
| 7,258,899 B1 | 8/2007 | Sharma et al. | |
| 7,288,091 B2 | 10/2007 | Nesbitt | |
| 7,300,859 B2 | 11/2007 | Mikhael et al. | |
| 7,390,326 B2 | 6/2008 | Nesbitt | |
| 7,566,333 B2 | 7/2009 | Van Wyk et al. | |
| 7,588,565 B2 | 9/2009 | Marchitto et al. | |
| 7,618,684 B2 | 11/2009 | Nesbitt | |
| 7,683,293 B2 | 3/2010 | Buzzi et al. | |
| 7,753,908 B2 | 7/2010 | Swanson | |
| 7,899,552 B2 | 3/2011 | Atanasoska et al. | |
| 7,955,637 B2 | 6/2011 | Nesbitt | |
| 7,967,839 B2 | 6/2011 | Flock et al. | |
| 7,976,544 B2 | 7/2011 | McClurken et al. | |
| 8,814,861 B2 | 8/2014 | Nesbitt | |
| 8,865,264 B2 | 10/2014 | Haack et al. | |
| 2001/0045351 A1 | 11/2001 | Koh et al. | |
| 2003/0036753 A1 | 2/2003 | Morgan et al. | |
| 2003/0158548 A1 | 8/2003 | Phan et al. | |
| 2003/0158549 A1 | 8/2003 | Swanson | |
| 2003/0229344 A1* | 12/2003 | Dycus | A61B 18/1445 606/51 |
| 2003/0236518 A1 | 12/2003 | Marchitto et al. | |
| 2004/0134770 A1 | 7/2004 | Petersen | |
| 2004/0210282 A1 | 10/2004 | Flock et al. | |
| 2005/0113828 A1 | 5/2005 | Shields et al. | |
| 2006/0116675 A1 | 6/2006 | McClurken et al. | |
| 2007/0029500 A1 | 2/2007 | Coulombe et al. | |
| 2007/0184208 A1 | 8/2007 | Sharma et al. | |
| 2008/0050291 A1 | 2/2008 | Nagasawa | |
| 2008/0063895 A1 | 3/2008 | Jun et al. | |
| 2008/0167398 A1 | 7/2008 | Patil et al. | |
| 2009/0102886 A1 | 4/2009 | Sieber et al. | |
| 2010/0069904 A1 | 3/2010 | Cunningham | |
| 2011/0270251 A1* | 11/2011 | Horner | A61B 18/1445 606/51 |
| 2012/0252709 A1 | 10/2012 | Felts et al. | |
| 2013/0116682 A1* | 5/2013 | Koo | A61B 18/14 606/41 |

FOREIGN PATENT DOCUMENTS

| | | |
|---|---|---|
| EP | 0991365 A4 | 4/2000 |
| JP | 62-130777 | 6/1987 |
| JP | 03-149797 | 6/1991 |
| JP | 8-243755 | 9/1996 |
| JP | 2000286094 A | 10/2000 |
| JP | 2001332399 A | 11/2001 |
| JP | 2003093869 A | 4/2003 |
| JP | 2005-522824 A | 7/2005 |
| JP | 2005276618 A | 10/2005 |
| JP | 2006114450 A | 4/2006 |
| JP | 2006310101 A | 11/2006 |
| JP | 2007188748 A | 7/2007 |
| JP | 2007207540 A | 8/2007 |
| JP | 2008041495 A | 2/2008 |
| JP | 2008071656 A | 3/2008 |
| WO | 9513313 A1 | 5/1995 |
| WO | 00/16706 A1 | 3/2000 |
| WO | 01/45862 A1 | 6/2001 |
| WO | 03/085693 A1 | 10/2003 |
| WO | 03/096880 A2 | 11/2003 |
| WO | 2004094306 A1 | 11/2004 |
| WO | 2009/146432 A1 | 12/2009 |
| WO | 2010008062 A1 | 1/2010 |

OTHER PUBLICATIONS

Japanese Notice of Final Rejection and Denial of Entry of Amendment (with English translation), dated Apr. 2, 2015, corresponding to Japanese Patent Application No. 2012-513022; 10 total pages.

Extended European Search Report issued in Appl. No. 10849146.5 dated Sep. 26, 2013; 6 pages.

Japanese Notice of Final Rejection and Denial of Entry of Amendment (with English translation), dated Jun. 2, 2015, corresponding to Japanese Patent Application No. 2013-502548; 15 total pages.

English translation of Japanese Notice of Reasons for Rejection, dated Feb. 18, 2014, corresponding to Japanese Patent Application No. 2013-502548; 6 pages.

English translation of Japanese Notice of Reasons for Rejection, dated Oct. 7, 2014, corresponding to Japanese Patent Application No. 2013-502548; 6 pages.

Australian Patent Examination Report No. 1, dated Apr. 17, 2014, corresponding to Australian Patent Application No. 2010349784; 3 pages.

European Communication dated Jun. 17, 2014, corresponding to European Patent Application No. 108491465; 6 pages.

European Communication/Examination Report dated Jul. 14, 2015, corresponding to European Patent Application No. 09 845 329.3; 8 pages.

(56) References Cited

OTHER PUBLICATIONS

European Search Report from Application No. EP 11 00 7711 completed Nov. 4, 2011.
European Search Report from Application No. EP 12191973.2 dated Mar. 20, 2013.
Extended European Search Report from Appl. No. EP 16196104 dated Apr. 7, 2017.
Chinese Office Action issued in Application No. CN 201610972039.9 dated Jul. 31, 2018, together with English language translation (15 pages).
Chinese Office Action issued in corresponding Appl. No. CN 201610972039.9 dated Apr. 8, 2019, together with English language translation (5 pages).

* cited by examiner

NON-STICK COATED ELECTROSURGICAL INSTRUMENTS AND METHOD FOR MANUFACTURING THE SAME

CROSS-REFERENCE TO RELATED APPLICATIONS

This application is a continuation in part application of U.S. application Ser. No. 14/926,553, filed on Oct. 29, 2015, the entire contents of which are incorporated by reference herein.

BACKGROUND

1. Technical Field

The present disclosure relates to an electrosurgical instrument and method for sealing tissue. More particularly, the present disclosure relates to an electrosurgical tool including opposing jaw members having sealing plates with improved non-stick coatings and methods for manufacturing the same.

2. Background of the Related Art

Electrosurgical forceps utilize mechanical clamping action along with electrical energy to effect hemostasis on the clamped tissue. The forceps (open, laparoscopic or endoscopic) include electrosurgical sealing plates which apply the electrosurgical energy to the clamped tissue. By controlling the intensity, frequency and duration of the electrosurgical energy applied through the sealing plates to the tissue, the surgeon can coagulate, cauterize, and/or seal tissue.

During an electrosurgical procedure, tissue sealing plates are used to apply electrosurgical energy to tissue. Because the sealing plates conduct electricity, care must be taken to electrically insulate the sealing plates from other electrically conductive components of the electrosurgical forceps and to limit and/or reduce many of the known undesirable effects related to tissue sealing, e.g., flashover, thermal spread, and stray current dissipation. Typically, tissue sealing surfaces are disposed on inner facing surfaces of opposing jaw members such that the tissue sealing surfaces are utilized to seal tissue grasped between the jaw members. Often, the manufacturing of jaw members requires the use of a two-shot molding process that includes a pre-shot overmold of insulative material (e.g., plastic) placed between the underside of the sealing plate and the steel structural support base of the jaw member to provide electrical insulation between the jaw member and the tissue sealing surface.

In the past, significant efforts have been directed to improvements in electrosurgical instruments and the like, with a view towards providing improved transmission of electrical energy to patient tissue in both an effective manner and to reduce the sticking of soft tissue to the instrument's surface during application. In general, such efforts have envisioned non-stick surface coatings, such as polymeric materials, e.g. polytetrafluoroethylene (PTFE, commonly sold under the trademark TEFLON®) for increasing the lubricity of the tool surface. However, these materials may interfere with the efficacy and efficiency of hemostasis and have a tendency to release from the instrument's substrate due to formation of microporosity, delamination, and/or abrasive wear, thus exposing underlying portions of the instrument to direct tissue contact and related sticking issues. In turn, these holes or voids in the coating lead to nonuniform variations in the capacitive transmission of the electrical energy to the tissue of the patient and may create localized excess heating, resulting in tissue damage, undesired irregular sticking of tissue to the electrodes and further degradation of the non-stick coating.

SUMMARY

In an aspect of the present disclosure, an electrosurgical instrument is provided. The electrosurgical instrument includes a handle having a shaft that extends therefrom, an end effector disposed at a distal end of the shaft, at least one electrode operably coupled to the end effector and adapted to couple to a source of electrosurgical energy, a titanium nitride coating covering at least a portion of the electrode, a chromium nitride coating covering at least a portion of the electrode, and a hexamethyldisiloxane plasma coating covering at least a portion of the chromium nitride coating. The chromium nitride coating may be disposed over a portion of the titanium nitride coating or all of the titanium nitride coating. The end effector may include a pair of opposing jaw members. At least one of the jaw members may include a support base and an electrical jaw lead, with the electrode coupled to the electrical jaw lead and the support base. The electrode may include a stainless steel layer and a hexamethyldisiloxane plasma coating may be disposed over at least a portion of the stainless steel layer.

An electrically insulative layer may be bonded to an underside of the sealing plate. The electrically insulative layer may be formed from a polyimide, a polycarbonate, a polyethylene, and/or any combinations thereof. In aspects, a titanium nitride coating is disposed on a topside of the stainless steel layer of the sealing plate, a chromium nitride coating is disposed over the titanium nitride coating, and the hexamethyldisiloxane plasma coating is disposed over the chromium nitride coating. The chromium nitride coating may be disposed over a portion of the titanium nitride coating or all of the titanium nitride coating. The end effector may additionally include an insulative housing disposed around the support base. A hexamethyldisiloxane plasma coating may also be disposed on the sealing plate and the insulative housing.

In another aspect of the present disclosure, an end effector for use with an electrosurgical instrument for sealing tissue is provided. The end effector may include a pair of opposing jaw members. At least one of the jaw members includes a support base, an electrical jaw lead, a sealing plate coupled to the electrical jaw lead and the support base, the sealing plate having a stainless steel layer, a titanium nitride coating disposed over at least a portion of the stainless steel layer, a chromium nitride coating disposed over at least a portion of the titanium nitride coating, and a hexamethyldisiloxane plasma coating disposed over at least one of the support base, the sealing plate, or the chromium nitride coating. The chromium nitride coating may be disposed over a portion of the titanium nitride coating or all of the titanium nitride coating.

The end effector may further include an electrically insulative layer disposed on at least a portion of an underside of the stainless steel layer. The electrically insulative layer may be formed from a polyimide, a polycarbonate, a polyethylene, and/or any combinations thereof. In aspects, a titanium nitride coating is disposed on a topside of the stainless steel layer of the sealing plate, a chromium nitride coating is disposed over at least a portion of the titanium nitride coating, and the hexamethyldisiloxane plasma coating is disposed over the chromium nitride coating. The end effector may additionally include an insulative housing disposed around the support base. A hexamethyldisiloxane plasma coating may also be disposed on the sealing plate and the insulative housing.

The hexamethyldisiloxane plasma coating may be disposed on each of the support base and the chromium nitride coating. Additionally, or alternatively, the end effector may include an insulative housing disposed around the support base and the hexamethyldisiloxane plasma coating may be disposed on the sealing plate and the insulative housing.

In another aspect of the present disclosure, a method of manufacturing an end effector assembly for use with an electrosurgical instrument is provided. The method includes forming a sealing plate, assembling a jaw member by affixing the sealing plate to a support base, and applying a hexamethyldisiloxane plasma coating to at least a portion of the assembled jaw member.

Forming a sealing plate includes stamping at least one sealing plate from a stainless steel sheet. Assembling the jaw member may further include bonding an electrically insulative layer to an underside of the sealing plate and/or overmolding an insulative material about the support base to secure the sealing plate thereto. The method may further include coupling an electrical lead to the sealing plate, the electrical lead configured to connect the sealing plate to an energy source. Additionally, or alternatively, the method may further include applying a titanium nitride coating to at least a portion of the assembled jaw member, applying a chromium nitride coating to at least a portion of the assembled jaw member and/or the titanium nitride coating, and applying a hexamethyldisiloxane plasma coating over at least a portion of the chromium nitride coating. Additionally, or alternatively, the method may further include forming a second seal plate, assembling a second jaw member by affixing the second sealing plate to a second support base, applying a hexamethyldisiloxane plasma coating to at least a portion of the second assembled jaw member, and assembling the end effector assembly by coupling the jaw member to the second jaw member.

In another aspect of the present disclosure, a method for manufacturing an electrosurgical instrument is provided. The method includes applying a titanium nitride coating to at least a portion of an electrically conductive surface, applying a chromium nitride coating to at least a portion of the titanium nitride coating, assembling the coated electrically conductive surface to a treatment member, and applying a hexamethyldisiloxane plasma coating over at least a portion of the treatment member. The chromium nitride coating may be disposed over a portion of the titanium nitride coating or all of the titanium nitride coating. Assembling the coated electrically conductive surface to the treatment member may include providing a support base to support the electrically conductive surface, and bonding an electrically insulative layer to an underside of the electrically conductive surface.

The method may further include overmolding an insulative material about the support base to secure the electrically conductive surface thereto. Additionally, or alternatively, the method may further include forming the electrically conductive surface by stamping the electrically conductive surface from a sheet of stainless steel. Additionally, or alternatively, the method may further include coupling an electrical lead to the electrically conductive surface, the electrical lead configured to connect the electrically conductive surface to an energy source.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
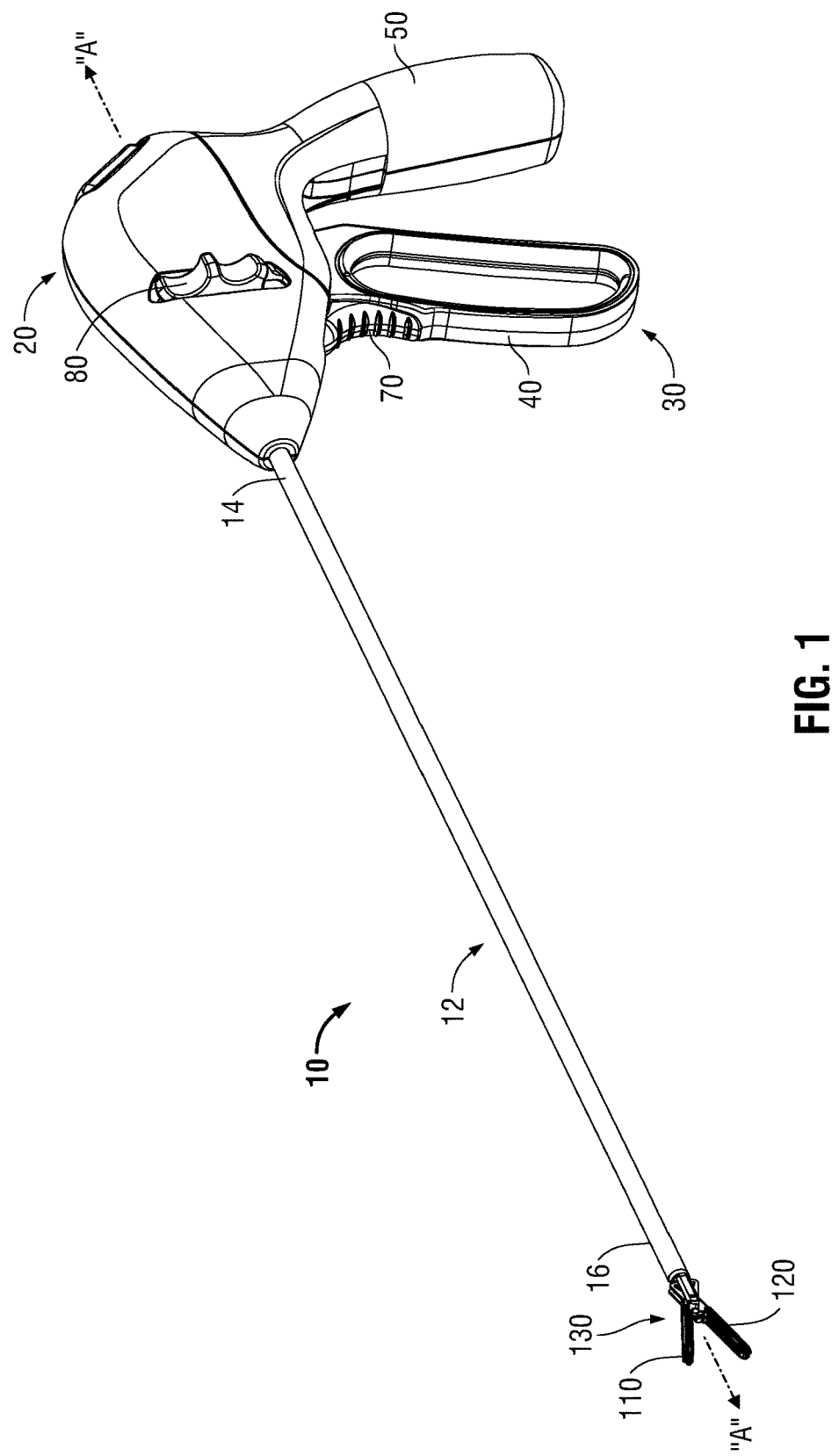
FIG. 1 is a perspective view of an endoscopic bipolar forceps in accordance with an aspect of the present disclosure.

Particular aspects of the present disclosure are described hereinbelow with reference to the accompanying drawings; however, it is to be understood that the disclosed aspects are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user. The term "clinician" refers to any medical professional (i.e., doctor, surgeon, nurse, or the like) performing a medical procedure involving the use of aspects described herein.

As described in more detail below with reference to the accompanying figures, the present disclosure is directed to electrosurgical instruments having a hexamethyldisiloxane ("HMDSO") plasma coating disposed on at least a portion thereof. The HMDSO plasma coating may be derived from HMDSO feed stock in plasma. For example, and without limitation, if pure argon is the media for the plasma and HMDSO is the feedstock, then the HMDSO plasma coating is polymeric with a structure close to [(CH3)2-Si—O]n. With increasing air content, a gradual change may be caused from organic polydimethylsiloxane-like coatings to inorganic, quartz-like deposits. For simplicity, the coating will be described herein as a HMDSO plasma coating. As described in further detail below, the coating may be further modified by introduction of other gasses or feedstocks.

In one aspect, the present disclosure is directed to opposing jaw members of a vessel sealer instrument having sealing plates with a HMDSO plasma coating deposited over a chromium nitride ("CrN") coating. Having a non-stick HMDSO plasma coating disposed on an outer surface of the sealing plate, jaw member, end effector, and/or any other portion of a surgical instrument has many advantages. For instance, HMDSO plasma coating, used in conjunction with CrN coating, operates to reduce the pitting of sealing plates as is common with arcing. The double coating provides durability against electrical and/or mechanical degradation of the sealing plates and the jaw members, as a whole, needed for long-term instrument durability. In particular, the additional HMDSO plasma coating reduces the sticking of tissue to the jaws or the surrounding insulating material of the end effector assembly and/or surgical instrument.

Another advantage of utilizing the HMDSO plasma coating, in conjunction with a CrN coating, is that the HMDSO plasma coating may be applied so thin as to have no functional effect on any tissue sealing properties. Specifically, the HMDSO plasma coating need not have any insulative effects. In one example, the resulting coating using HMDSO as a feedstock in the plasma is silicone oxide matrix with a functionalized surface, in some instances that of surfaced with —CH3.

Turning now to FIG. 1, an instrument generally identified as forceps 10 is for use with various surgical procedures and includes a housing 20, a handle assembly 30, a rotating assembly 80, a trigger assembly 70, and an end effector assembly 130 that mutually cooperate to grasp, seal, and divide tubular vessels and vascular tissues. Forceps 10 includes a shaft 12 extending from a distal end of the housing 20. The shaft 12 has a distal end 16 dimensioned to mechanically engage the end effector assembly 130 and a proximal end 14 that mechanically engages the housing 20.

The end effector assembly 130 includes opposing jaw members 110 and 120, which cooperate to effectively grasp tissue for sealing purposes. Both jaw members 110 and 120 pivot relative to one another about a pivot pin (not shown). Alternatively, jaw member 110 may be movable relative to a stationary jaw member 120, and vice versa. The jaw members 110 and 120 may be curved to facilitate manipulation of tissue and to provide better "line-of-sight" for accessing targeted tissues.

Examples of forceps are shown and described in commonly-owned U.S. application Ser. No. 10/369,894 entitled "VESSEL SEALER AND DIVIDER AND METHOD MANUFACTURING SAME" and commonly-owned U.S. application Ser. No. 10/460,926 (now U.S. Pat. No. 7,156, 846) entitled "VESSEL SEALER AND DIVIDER FOR USE WITH SMALL TROCARS AND CANNULAS," the entire contents of each of which are incorporated by reference herein.

Figure 2:
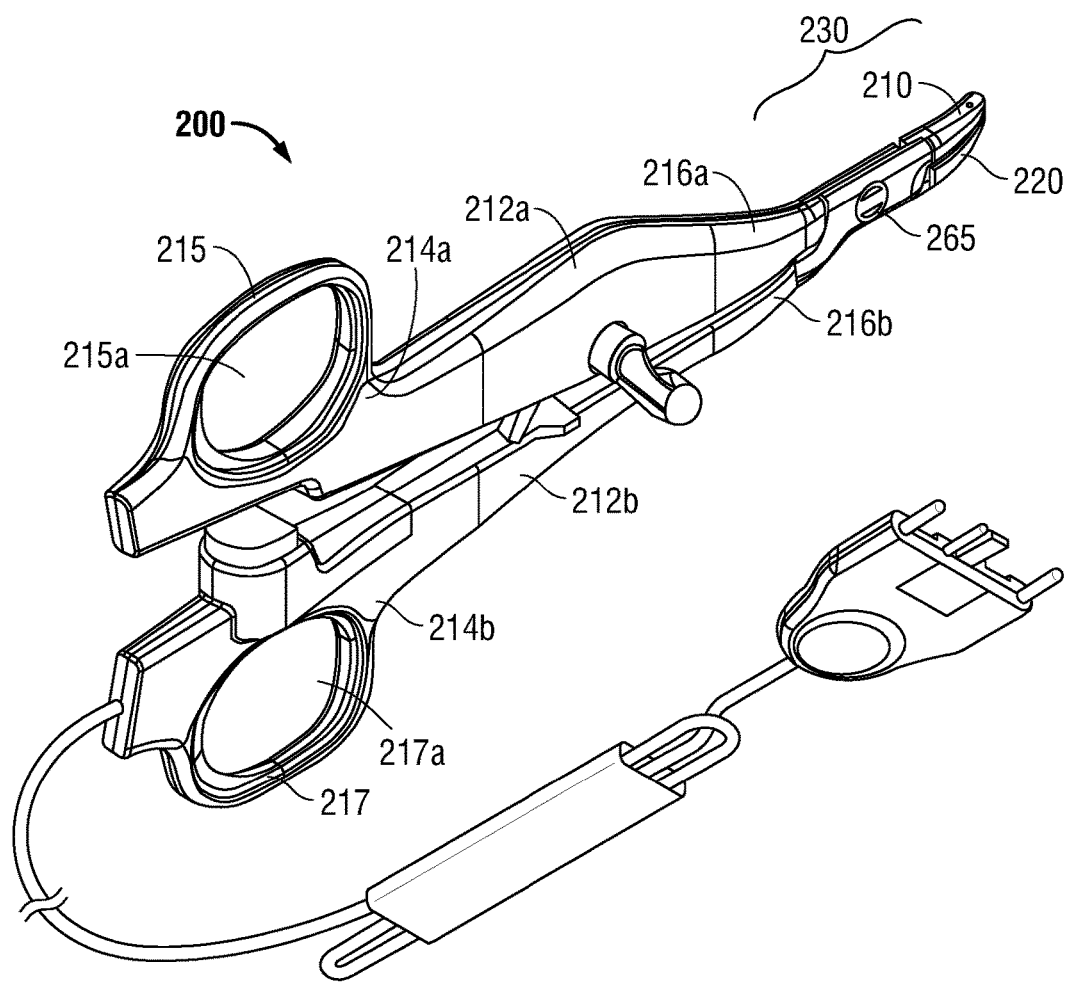
FIG. 2 is a perspective view of an open bipolar forceps according to an aspect of the present disclosure.

With regard to FIG. 2, an open forceps 200 for use with various surgical procedures is shown. Forceps 200 includes a pair of opposing shafts 212a and 212b having an end effector assembly 230 attached to the distal ends 216a and 216b thereof, respectively. End effector assembly 230 includes pair of opposing jaw members 210 and 220 that are pivotably connected about a pivot pin 265 and that are movable relative to one another to grasp tissue. Each shaft 212a and 212b includes a handle 215 and 217, respectively, disposed at the proximal end 214a and 214b thereof and that each define a finger hole 215a and 217a, respectively, therethrough for receiving a finger of the user. Finger holes 215a and 217a facilitate movement of the shafts 212a and 212b relative to one another to pivot the jaw members 210 and 220 between an open position, wherein the jaw members 210 and 220 are disposed in spaced relation relative to one another, and a clamping or closed position, wherein the jaw members 210 and 220 cooperate to grasp tissue therebetween.

Figure 3A:
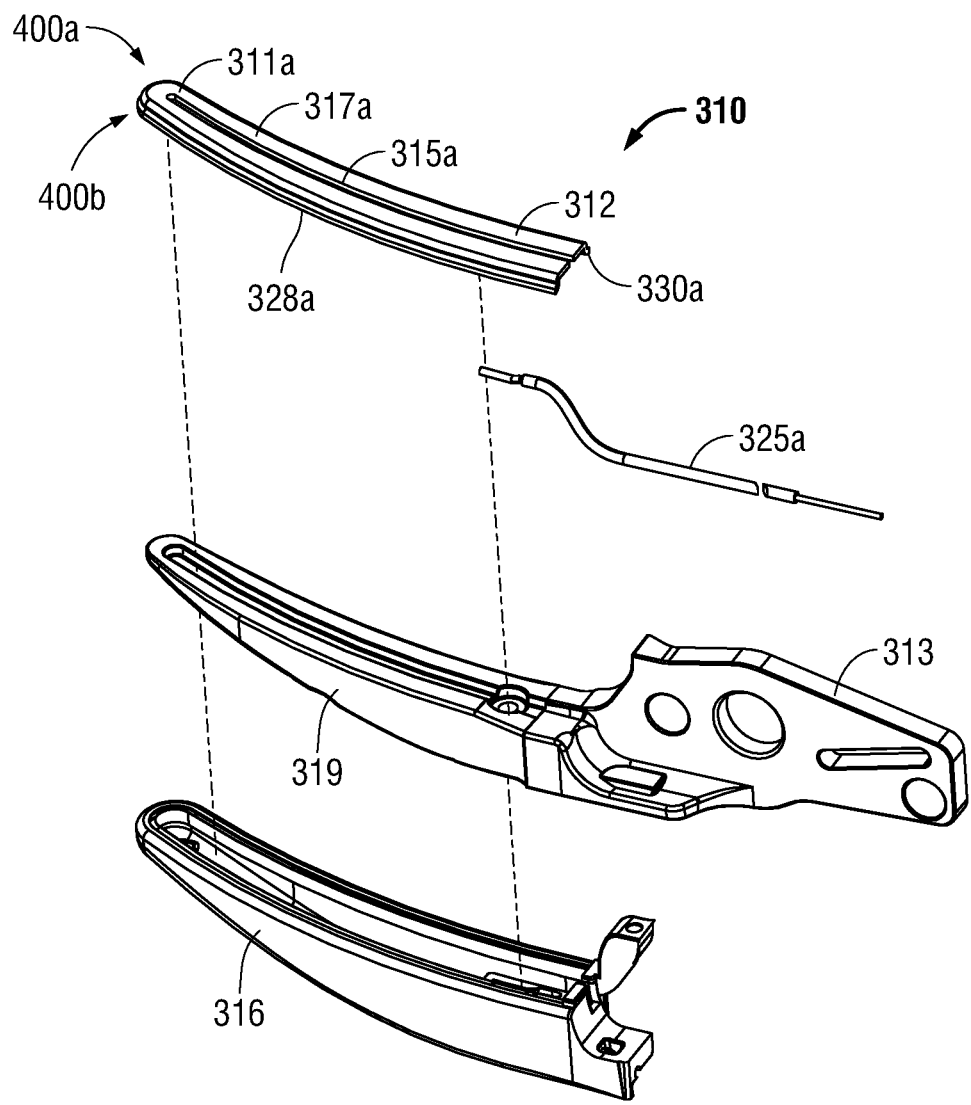
FIGS. 3A and 3B are exploded views of opposing jaw members according to an aspect of the present disclosure.
Figure 3B:
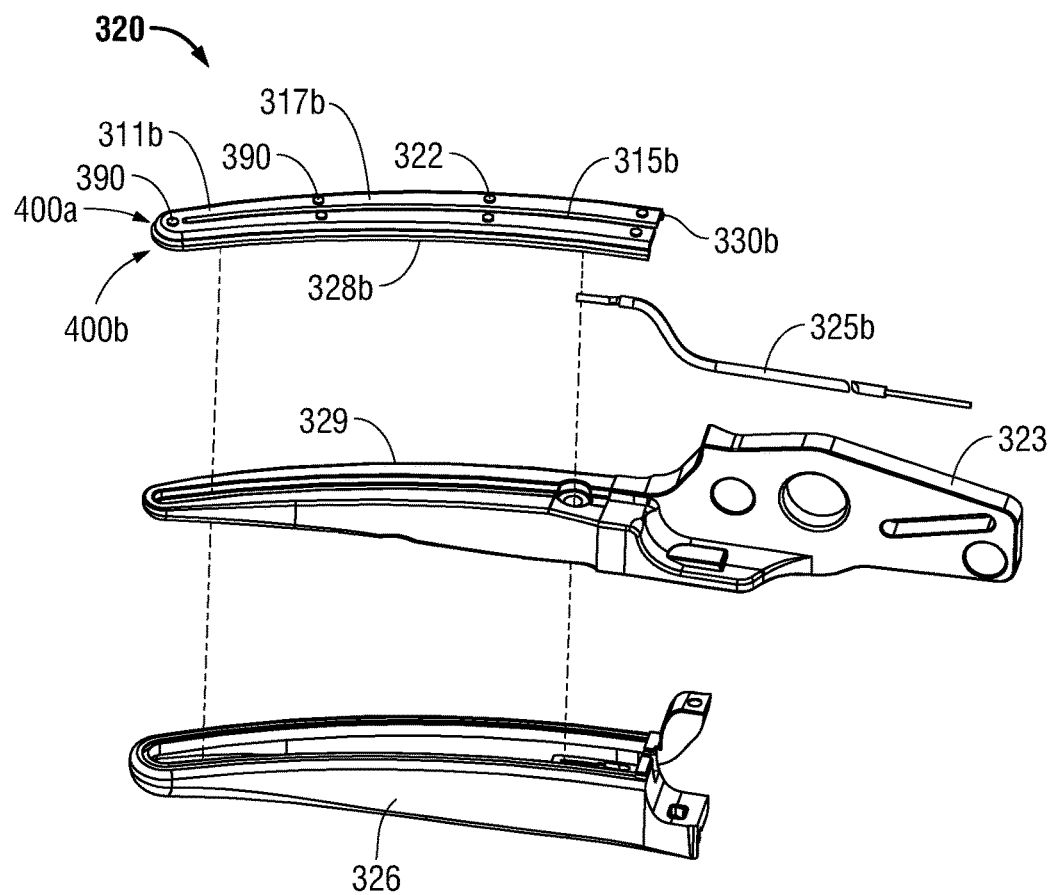

FIGS. 3A and 3B are perspective views of opposing jaw members 310 and 320 according to one aspect of the present disclosure which may be utilized with both endoscopic forceps 10 (FIG. 1) and open forceps 200 (FIG. 2). Similar to jaw members 110 and 120 (FIG. 1) and jaw members 210 and 220 (FIG. 2), each of the jaw members 310 and 320 include: sealing plates 312 and 322 (also referred to herein as electrically conductive plate, conductive plates, and/or electrodes), respectively; electrical jaw leads 325a and 325b, respectively; and support bases 319 and 329 that extend distally from flanges 313 and 323, respectively.

Each of sealing plates 312 and 322 include an underside 328a and 328b, respectively, that may include a respective electrically insulative layer 330a and 330b bonded thereto or otherwise disposed thereon. Electrically insulative layers 330a and 330b operate to electrically insulate sealing plates 312 and 322, respectively, from support bases 319 and 329, respectively. Further, electrically insulative layers 330a and 330b operate to prevent or slow the onset of corrosion of sealing plates 312 and 322, respectively, at least on the undersides 328a, 328b thereof. In one embodiment, electrically insulative layers 330a and 330b may be formed from polyimide. However, in other embodiments, any suitable electrically insulative material may be utilized, such as polycarbonate, polyethylene, etc.

Additionally, each of jaw members 310 and 320 include an outer surface 311a and 311b, respectively, that may include a respective chromium nitride ("CrN") coating 400a and/or hexamethyldisiloxane ("HMDSO") plasma coating 400b disposed, or otherwise deposited, thereon. CrN coating 400a and/or HMDSO plasma coating 400b may be disposed on selective portions of either of jaw member 310 and 320, or may be disposed on the entire outer surfaces 311a and 311b. In one embodiment, CrN coating 400a and HMDSO plasma coating 400b is disposed on an outer surface 317a and/or 317b of sealing plates 312 and 322, respectively. HMDSO plasma coating 400b, used in conjunction with CrN coating 400a, operates to reduce the pitting of sealing plates 312 and 322 as is common with arcing. The double coating provides durability against electrical and/or mechanical degradation of the sealing plates 312 and 322 and the jaw members 310 and 320 as a whole, needed for long-term instrument durability. In particular, the additional HMDSO plasma coating 400b reduces the sticking of tissue to the jaw members 310 and 320 or the surrounding insulating material.

Support bases 319 and 329 are configured to support electrically conductive sealing plates 312 and 322 thereon. Sealing plates 312 and 322 may be affixed atop the support bases 319 and 329, respectively, by any suitable method including but not limited to snap-fitting, overmolding, stamping, ultrasonic welding, etc. The support bases 319 and 329 and sealing plates 312 and 322 are at least partially encapsulated by insulative housings 316 and 326, respectively, by way of an overmolding process to secure sealing plates 312 and 322 to support bases 319 and 329, respectively. The sealing plates 312 and 322 are coupled to electrical jaw leads 325a and 325b, respectively, via any suitable method (e.g., ultrasonic welding, crimping, soldering, etc.). Electrical jaw lead 325a supplies a first electrical potential to sealing plate 312 and electrical jaw lead 325b supplies a second electrical potential to opposing sealing plate 322.

Jaw member 320 (and/or jaw member 310) may also include a series of stop members 390 disposed on the topside surface 317a (the inner facing surface) of sealing plate 312 to facilitate gripping and manipulation of tissue and to define a gap between opposing jaw members 310 and 320 during sealing and cutting of tissue. The series of stop members 390 are applied onto the sealing plate 312 during manufacturing. Some or all of the stop members 390 may be coated with the CrN coating 400a and/or the HMDSO plasma coating 400b, or alternatively may be disposed on top of the CrN coating 400a and/or the HMDSO plasma coating 400b. Further, the sealing plates 312 and 322 may include longitudinally-oriented knife slots 315a and 315b, respectively, defined therethrough for reciprocation of a knife blade (not shown). The electrically insulative layers 330a and 330b disposed on the undersides 328a and 328b, respectively, of sealing plates 312 and 322, respectively, allow for various blade configurations such as, for example, T-shaped blades or I-shaped blades that may contact the underside of the sealing plate (and/or insulating layer) during reciprocation through knife slots 315a, 315b. That is, the electrically insulative layers 330a, 330b operate to protect both the knife blade and the undersides 328a and 328b of the sealing plates 312 and 322, respectively, from damage or wearing. Further, in the instance that an electrically conductive knife blade is utilized (e.g., for electric tissue cutting), the electrically insulative layers 330a, 330b help to electrically insulate the sealing plates 312, 322 from the electrically conductive knife blade.

Figure 4A:
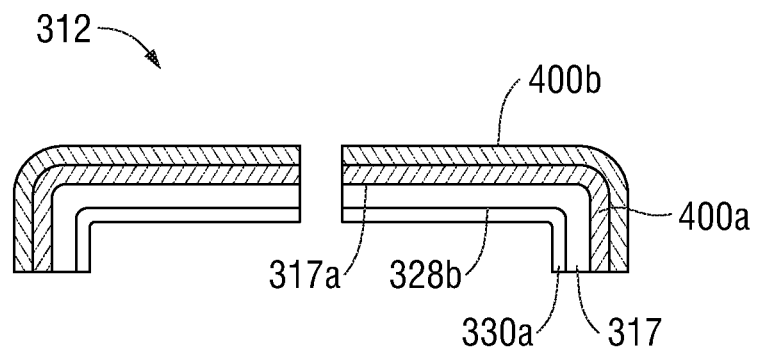
FIG. 4A is a front cross sectional view of a sealing plate according to an aspect of the present disclosure.

Turning now to FIG. 4A, a front cross sectional view of sealing plate 312 is shown and will be described. Sealing plate 312 has a stainless steel layer 317, an electrically insulative layer 330a, a CrN coating 400a, and an HMDSO plasma coating 400b. Sealing plate 312 may be formed by bonding electrically insulative layer 330a to the underside 328b of stainless steel layer 317, coating at least the upper surface 317a of the stainless steel layer 317 with a CrN coating 400a, and coating at least a portion of the CrN coating 400a and/or the stainless steel layer 317 with an HMDSO plasma coating 400b. Bonding electrically insulative layer 330a to stainless steel layer 317 may be accomplished by any suitable method including, but not limited to, applying adhesive between electrically insulative layer 330a and stainless steel layer 317, using heat treatment to bond electrically insulative layer 330a to stainless steel layer 317, and/or any combinations thereof. Electrically insulative layer 430a may have a thickness ranging from about 0.001 inches to about 0.005 inches. Sealing plate 312, which includes stainless steel layer 317, electrically insulative layer 330a, CrN coating 400a and HMDSO plasma coating 400b, may have a thickness ranging from about 0.005 inches to about 0.010 inches.

Sealing plate 312 may be formed by bonding a sheet of electrically insulative to a sheet of stainless steel and coating the sheet of stainless steel with at least one of a CrN coating and/or an HMDSO plasma coating. Once the two materials are bonded together, and the stainless steel sheet is coated with one or both of the CrN layer and/or the HMDSO plasma layer, sealing plate 312 may be formed by stamping, machining, or any other suitable method used to form a sealing plate.

Figure 4B:
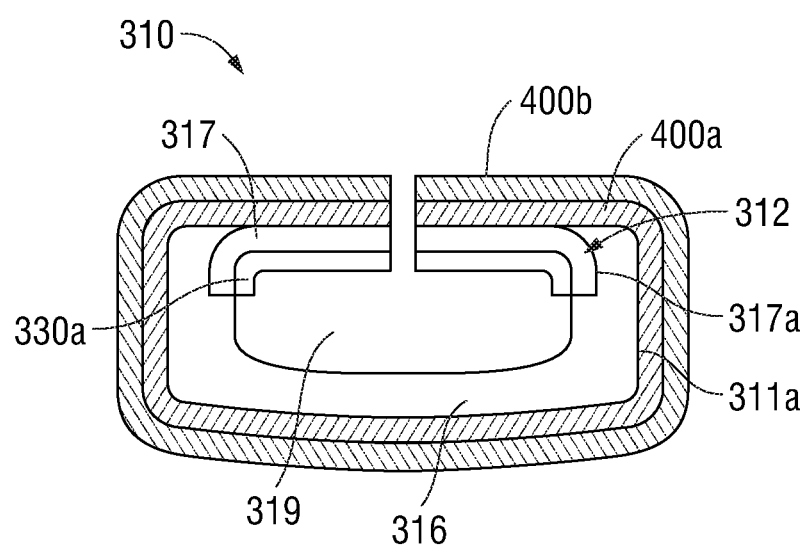
FIG. 4B is a front cross sectional view of a jaw member according to an aspect of the present disclosure.

Turning now to FIG. 4B, a front cross sectional view of jaw member 310 is shown and will be described. Jaw member 310 includes sealing plate 312 having a stainless steel layer 317 and, optionally, an electrically insulative layer 330a. Sealing plate 312 is affixed to support base 319 via any suitable process. Additionally, with sealing plate 312 secured to support base 319, the combined sealing plate 312 and support base 319 is secured to insulative housing 316 via any suitable process. A CrN coating 400a is disposed over the outer surface 311a of the assembled sealing plate 312, support base 319, and insulative housing 316. Additionally, an HMDSO plasma coating 400b is disposed over the CrN coating 400a. As described above, in embodiments it may be useful to coat only a partial outer surface 311a of the jaw member 310 or include thicker layers of the CrN coating 400a and/or the HMDSO plasma coating 400b on different portions of the outer surface 311a of the jaw member 310.

Additionally, or alternatively, in embodiments, the sealing plates 312 may be coated in the manner described above with respect to FIG. 4A and the outer surface 311a of the jaw member 310 may also be coated with the CrN coating 400a and/or the HMDSO plasma coating 400b.

Figure 5:
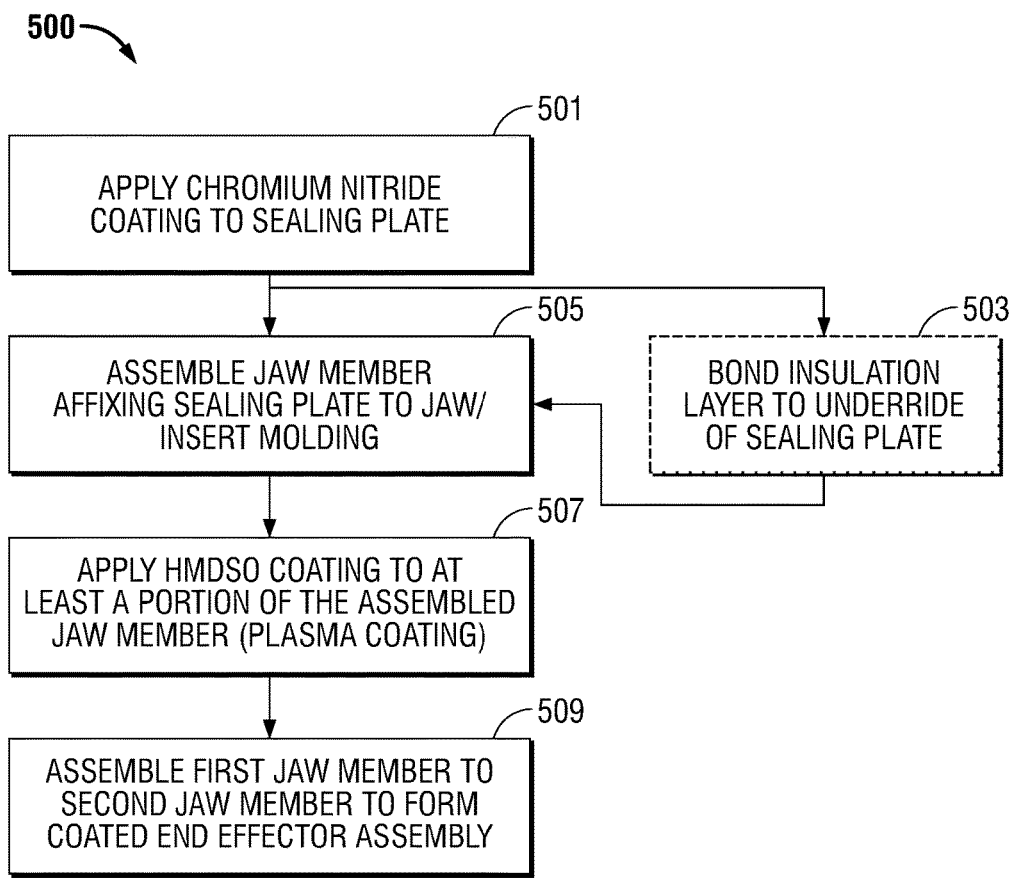
FIG. 5 is a flow chart illustrating a method of manufacturing an end effector assembly for use with an electrosurgical instrument according to an aspect of the present disclosure.

Turning now to FIG. 5, a method for manufacturing an HMDSO plasma coated end effector assembly is illustrated and will be described as method 500. Method 500 begins in step 501 where a CrN coating and/or an HMDSO plasma coating is applied to a sealing plate.

The HMDSO plasma coating may be applied using a system or process which includes a plasma device that is coupled to a power source, an ionizable media source and a precursor or pre-ionization source similar to the system described in U.S. Patent Publication No. 2013/0116682, filed on Nov. 9, 2011, the contents of which is incorporated by reference herein in its entirety. The power source may include any suitable components for delivering power or matching impedance to the plasma device. More particularly, the power source may be any radio frequency generator or other suitable power source capable of producing electrical power to ignite and sustain the ionizable media to generate a plasma effluent.

Plasmas are generated using electrical energy that is delivered as either direct current (DC) electricity or alternating current (AC) electricity, in either continuous or pulsed modes, at frequencies from about 0.1 hertz (Hz) to about 100 gigahertz (GHz), including radio frequency bands ("RF", from about 0.1 MHz to about 100 MHz) and microwave bands ("MW", from about 0.1 GHz to about 100 GHz), using appropriate generators, electrodes, and antennas. AC electrical energy may be supplied at a frequency from about 0.1 MHz to about 2,450 MHz, in embodiments from about 1 MHz to about 160 MHz. The plasma may also be ignited by using continuous or pulsed direct current (DC) electrical energy or continuous or pulsed RF electrical energy or combinations thereof. Choice of excitation frequency, the workpiece, as well as the electrical circuit that is used to deliver electrical energy to the circuit affects many properties and requirements of the plasma. The performance of the plasma chemical generation, the gas or liquid feedstock delivery system and the design of the electrical excitation circuitry are interrelated, as the choices of operating voltage, frequency and current levels, as well as phase, effect the electron temperature and electron density. Further, choices of electrical excitation and plasma device hardware also determine how a given plasma system responds dynamically to the introduction of new ingredients to the host plasma gas or liquid media. The corresponding dynamic adjustment of the electrical drive, such as via dynamic match networks or adjustments to voltage, current, or excitation frequency may be used to maintain controlled power transfer from the electrical circuit to the plasma.

Continuing with reference to FIG. 5, the sealing plate may be formed of stainless steel which is stamped from a large stainless steel sheet which has already been coated with any of the coatings described herein. Method 500 may optionally also include step 503 where an insulative layer is bonded or otherwise affixed to an underside of the sealing plate. In some aspects, the insulative layer may be bonded to an entire sheet of stainless steel and the sealing plate is stamped from the sheet of stainless steel after the insulative layer is bonded to the sheet of stainless steel.

In step 505, the jaw member is assembled. Specifically, in step 505 the coated sealing plate is affixed to a support base and/or an insulative housing. In 505, the jaw member may be assembled via any suitable process including insert molding. In step 507, an HMDSO plasma coating is applied to at least a portion of the assembled jaw member. Step 507 may be carried out via plasma coating. The HMDSO plasma coating may be enhanced by the addition of oxygen or fluorine in the plasma and deposition. Any or all of steps 501-507, described above, are repeated to assemble an opposing (second) jaw member. In step 509, the first assembled jaw member and the second assembled jaw member are assembled to form a coated end effector assembly. That is, the first assembled jaw member is pivotably coupled to the second assembled jaw member to create the assembled coated end effector assembly.

Figure 6:
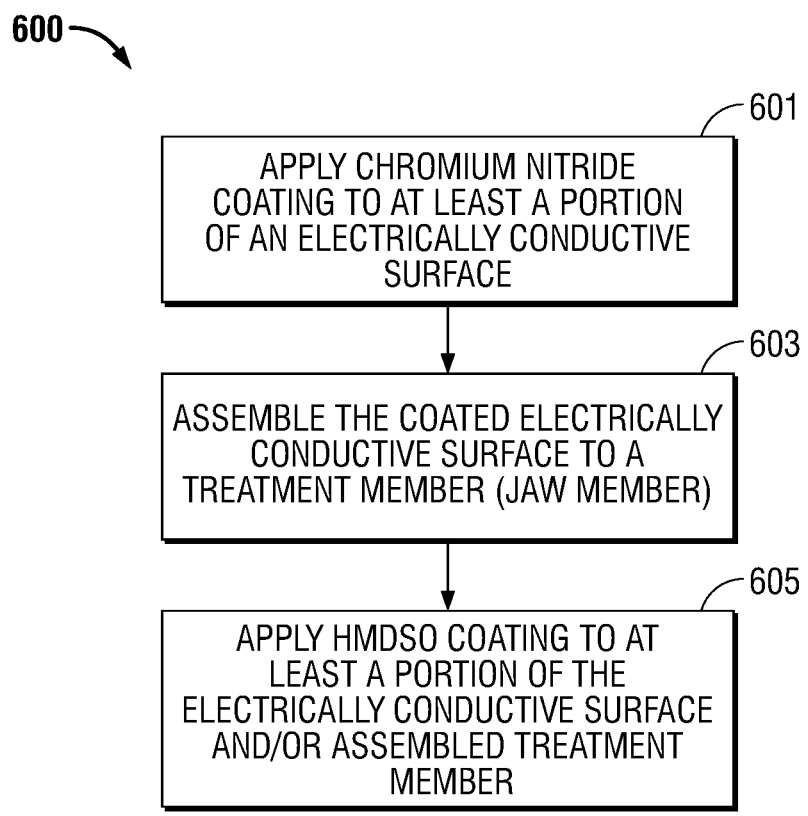
FIG. 6 is a flow chart illustrating a method of manufacturing an electrosurgical instrument according to an aspect of the present disclosure.

Turning now to FIG. 6, a method for manufacturing an HMDSO plasma coated end instrument is illustrated and will be described as method 600. Method 600 begins in step 601 where a CrN coating is applied to at least a portion of an electrically conductive surface. The electrically conductive surface may be a sealing plate which may be formed of stainless steel. The stainless steel may be stamped from a large stainless steel sheet which has already been coated with any of the coatings described herein. Method 600 may optionally also include a step where an insulative layer is bonded or otherwise affixed to an underside of the electrically conductive surface. In some aspects, the insulative layer may be bonded to an entire sheet of stainless steel and the electrically conductive surface is stamped from the sheet of stainless steel after the insulative layer is bonded to the sheet of stainless steel.

In step 603, a treatment member is assembled. The treatment member may be a jaw member as previously described herein. Specifically, in step 603 the coated electrically conductive surface is affixed to a support base and/or an insulative housing. In 603, the treatment member may be assembled via any suitable process including insert molding. In step 605, an HMDSO plasma coating is applied to at least a portion of the electrically conductive surface and/or the assembled treatment member. Step 605 may be carried out via plasma coating the electrically conductive surface and/or the assembled treatment member. The HMDSO plasma coating may be enhanced by the addition of oxygen or fluorine in the plasma and deposition. Any or all of steps 601-605, described above, may be repeated to assemble an opposing (second) treatment member.

As described in more detail below with reference to the accompanying figures, another aspect of the present disclosure is directed to electrosurgical instruments having a HMDSO plasma coating disposed on at least a portion thereof, in combination with a portion of the instrument being coated with CrN and a portion of the instrument being coated with titanium nitride ("TiN"). As described above, the HMDSO plasma coating may be derived from HMDSO feed stock in plasma. For example, and without limitation, if pure argon is the media for the plasma and HMDSO is the feedstock, then the HMDSO plasma coating is polymeric with a structure close to [(CH3)2-Si—O]n. With increasing air content, a gradual change may be caused from organic polydimethylsiloxane-like coatings to inorganic, quartz-like deposits. For simplicity, the coating will be described herein as a HMDSO plasma coating. As described in further detail below, the coating may be further modified by introduction of other gasses or feedstocks.

In one aspect, the present disclosure is directed to opposing jaw members of a vessel sealer instrument having sealing plates with a HMDSO plasma coating deposited over at least a portion of CrN coating, and the CrN coating deposited over at least a portion of a TiN coating. Having a non-stick HMDSO plasma coating disposed on an outer surface of the sealing plate, jaw member, end effector, and/or any other portion of a surgical instrument has many advantages. For instance, HMDSO plasma coating, used in conjunction with CrN coating and TiN coating operates to reduce the pitting of sealing plates as is common with electrosurgical arcing. The multiple layered coating provides durability against electrical and/or mechanical degradation of the sealing plates and the jaw members, as a whole, needed for long-term instrument durability. In particular, the additional HMDSO plasma coating in combination with a TiN and CrN coating reduces the sticking of tissue to the jaws or the surrounding insulating material of the end effector assembly and/or surgical instrument.

Figure 8A:
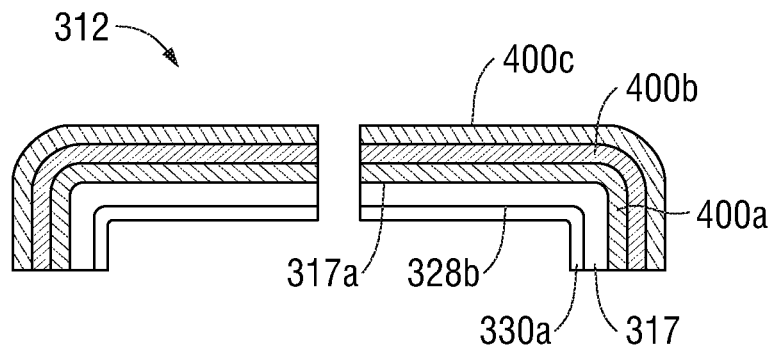
FIG. 8A is a front cross sectional view of a sealing plate according to an aspect of the present disclosure.
Figure 8B:
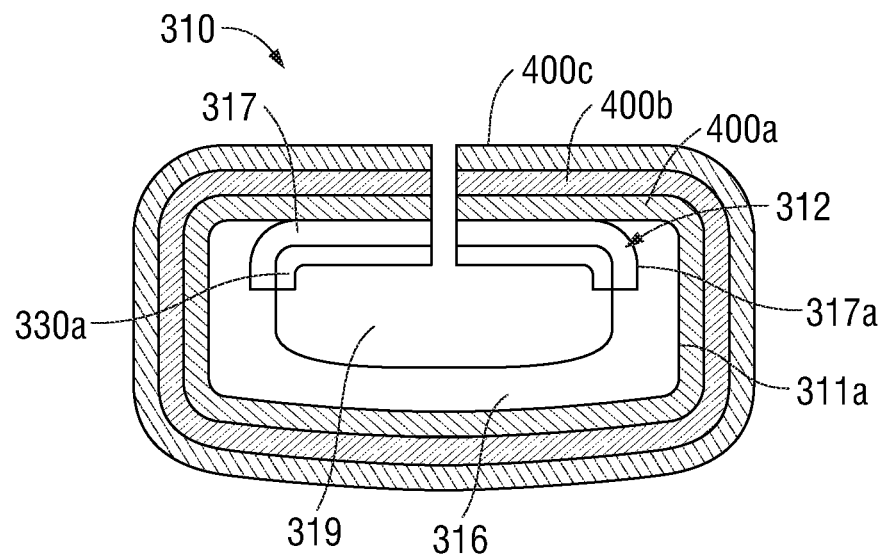
FIG. 8B is a front cross sectional view of a jaw member according to an aspect of the present disclosure.

Turning now to FIGS. 8A-8B, aspects of an electrosurgical instrument including a multi-layered coating comprising any of HMDSO, CrN, or TiN will be described. Each of jaw members 310 and 320 includes an outer surface 311*a* and 311*b*, respectively, that may include a respective TiN coating 400*c*, CrN coating 400*a*, and/or HMDSO plasma coating 400*b* disposed, or otherwise deposited, thereon. TiN coating 400*c*, CrN coating 400*a*, and/or HMDSO plasma coating 400*b* may be disposed on selective portions of either or both jaw members 310 and 320, or may be disposed on the entire outer surfaces 311*a* and 311*b*. In one embodiment, TiN coating 400*c*, CrN coating 400*a*, and HMDSO plasma coating 400*b* is disposed on an outer surface 317*a* and/or 317*b* of sealing plates 312 and 322, respectively. As mentioned above, HMDSO plasma coating 400*b*, used in conjunction with CrN coating 400*a* and TiN coating 400*c*, operates to reduce the pitting of sealing plates 312 and 322 as is common with arcing. The triple coating provides durability against electrical and/or mechanical degradation of the sealing plates 312 and 322 and the jaw members 310 and 320 as a whole, which improves long-term instrument durability. In particular, the additional HMDSO plasma coating 400*b* over the CrN coating 400*a* and the TiN coating 400*c* reduces the sticking of tissue to the jaw members 310 and 320 or the surrounding insulating material.

Support bases 319 and 329 are configured to support electrically conductive sealing plates 312 and 322 thereon. Sealing plates 312 and 322 may be affixed atop the support bases 319 and 329, respectively, by any suitable method including but not limited to snap-fitting, overmolding, stamping, ultrasonic welding, etc. The support bases 319 and 329 and sealing plates 312 and 322 are at least partially encapsulated by insulative housings 316 and 326, respectively, by way of an overmolding process to secure sealing plates 312 and 322 to support bases 319 and 329, respectively. The sealing plates 312 and 322 are coupled to electrical jaw leads 325a and 325b, respectively, via any suitable method (e.g., ultrasonic welding, crimping, soldering, etc.). Electrical jaw lead 325a supplies a first electrical potential to sealing plate 312 and electrical jaw lead 325b supplies a second electrical potential to opposing sealing plate 322.

Jaw member 320 (and/or jaw member 310) may also include a series of stop members 390 disposed on the inner facing surface 317a of sealing plate 312 to facilitate gripping and manipulation of tissue and to define a gap between opposing jaw members 310 and 320 during sealing and cutting of tissue. The series of stop members 390 are applied onto the sealing plate 312 during manufacturing. Some or all of the stop members 390 may be coated with the TiN coating 400c, CrN coating 400a, and/or the HMDSO plasma coating 400b, or alternatively may be disposed on top of the TiN coating 400c, CrN coating 400a, and/or the HMDSO plasma coating 400b. Further, the sealing plates 312 and 322 may include longitudinally-oriented knife slots 315a and 315b, respectively, defined therethrough for reciprocation of a knife blade (not shown). The electrically insulative layers 330a and 330b disposed on the undersides 328a and 328b, respectively, of sealing plates 312 and 322, respectively, allow for various blade configurations such as, for example, T-shaped blades or I-shaped blades that may contact the underside of the sealing plate (and/or insulating layer) during reciprocation through knife slots 315a, 315b. That is, the electrically insulative layers 330a, 330b operate to protect both the knife blade and the undersides 328a and 328b of the sealing plates 312 and 322, respectively, from damage or wearing. Further, in the instance that an electrically conductive knife blade is utilized (e.g., for electric tissue cutting), the electrically insulative layers 330a, 330b help to electrically insulate the sealing plates 312, 322 from the electrically conductive knife blade.

Figure 7A:
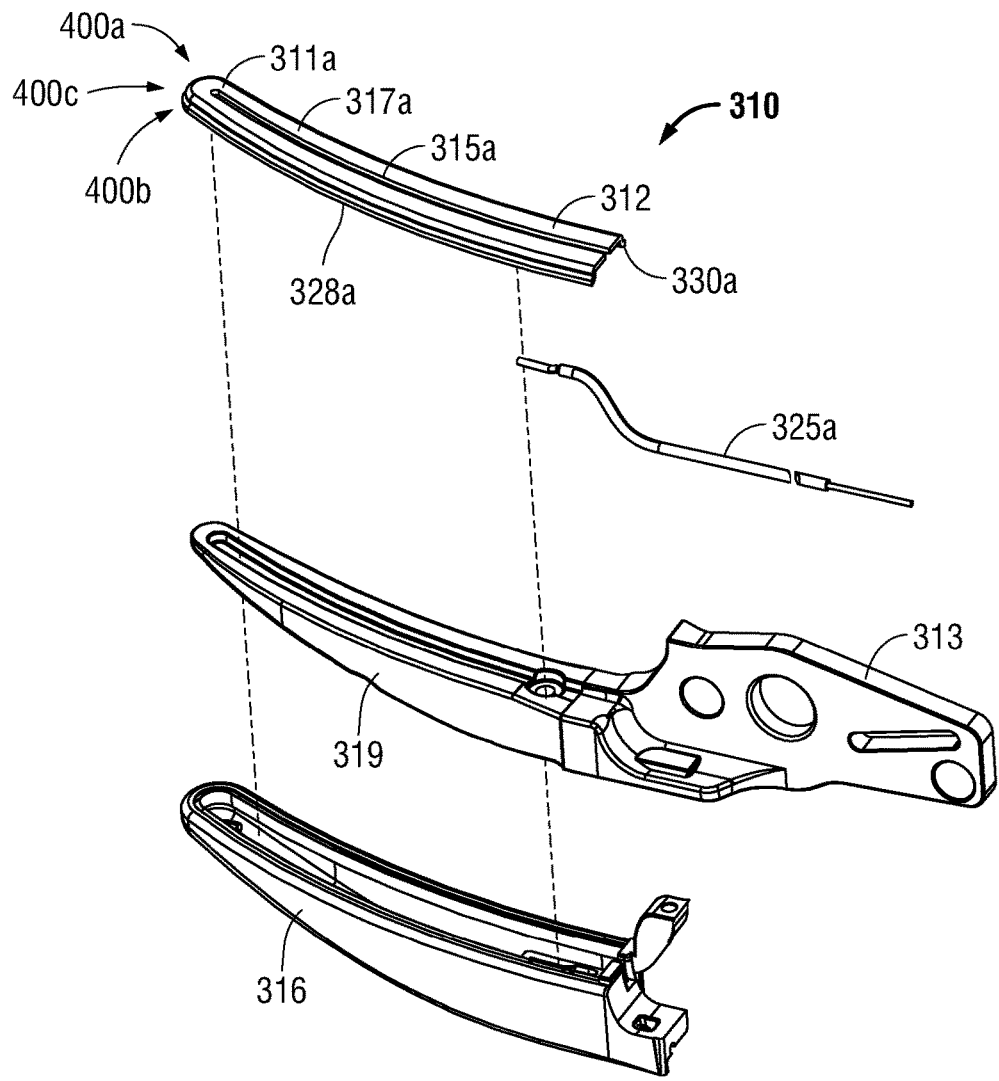
FIGS. 7A and 7B are exploded views of opposing jaw members according to an aspect of the present disclosure.
Figure 7B:
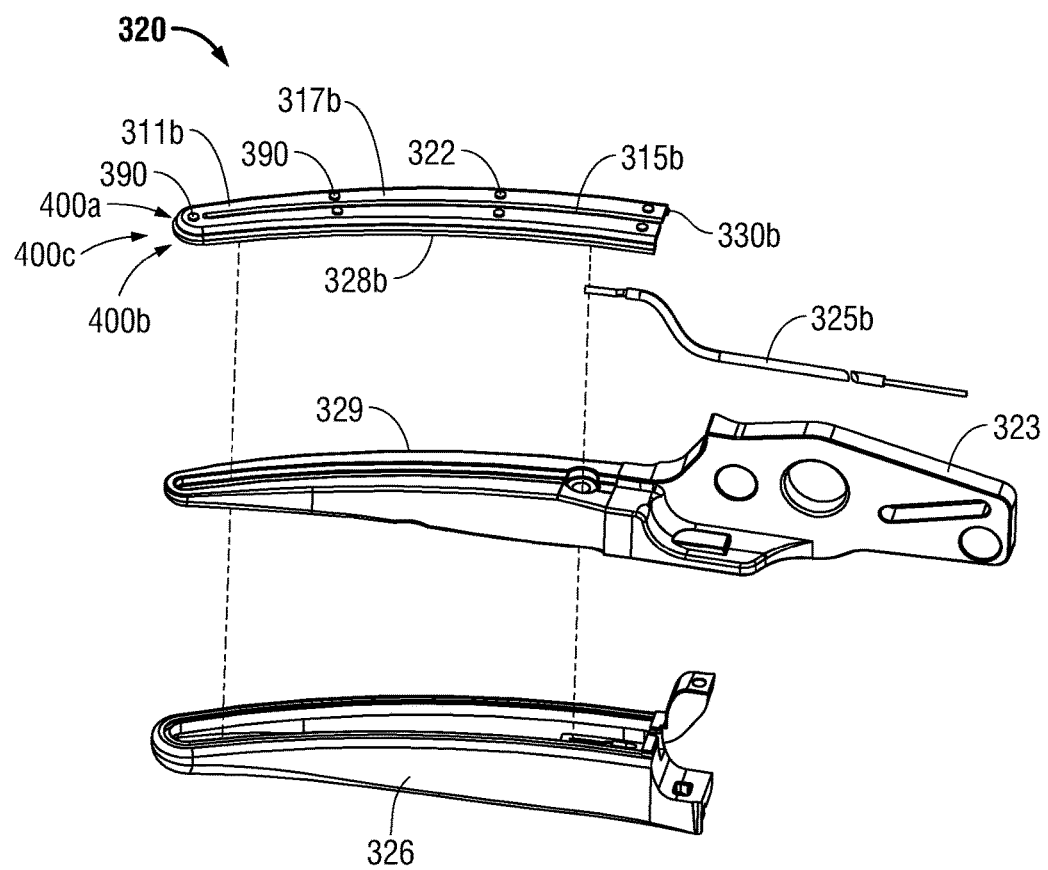

Turning now to FIG. 7A, a front cross sectional view of sealing plate 312 is shown and will be described. Sealing plate 312 has a stainless steel layer 317, an electrically insulative layer 330a, a TiN coating 400c, a CrN coating 400a, and an HMDSO plasma coating 400b. Sealing plate 312 may be formed by bonding electrically insulative layer 330a to the underside 328b of stainless steel layer 317, coating at least the upper surface 317a of the stainless steel layer 317 with a TiN coating 400c, coating at least a portion of the TiN coating 400c and/or the stainless steel layer 317 with a CrN coating 400a, and coating at least a portion of the CrN coating 400a and/or the stainless steel layer 317 with an HMDSO plasma coating 400b. Bonding electrically insulative layer 330a to stainless steel layer 317 may be accomplished by any suitable method including, but not limited to, applying adhesive between electrically insulative layer 330a and stainless steel layer 317, using heat treatment to bond electrically insulative layer 330a to stainless steel layer 317, and/or any combinations thereof. Electrically insulative layer 430a may have a thickness ranging from about 0.001 inches to about 0.005 inches. Sealing plate 312, which includes stainless steel layer 317, electrically insulative layer 330a, TiN coating 400c, CrN coating 400a, and HMDSO plasma coating 400b, may have a thickness ranging from about 0.005 inches to about 0.010 inches.

Sealing plate 312 may be formed by bonding a sheet of electrically insulative material to a sheet of stainless steel and coating the sheet of stainless steel with at least one of a TiN coating, a CrN coating, and/or an HMDSO plasma coating. Once the materials are bonded together, and the stainless steel sheet is coated with one, two, or all three of the TiN layer, the CrN layer, and/or the HMDSO plasma layer, sealing plate 312 may be formed by stamping, machining, or any other suitable method used to form a sealing plate.

Turning now to FIG. 8B, a front cross sectional view of jaw member 310 is shown and will be described. Jaw member 310 includes sealing plate 312 having a stainless steel layer 317 and, optionally, an electrically insulative layer 330a. Sealing plate 312 is affixed to support base 319 via any suitable process. Additionally, with sealing plate 312 secured to support base 319, the combined sealing plate 312 and support base 319 is secured to insulative housing 316 via any suitable process. A TiN coating 400c and/or a CrN coating 400a is disposed over the outer surface 311a of the assembled sealing plate 312, support base 319, and insulative housing 316. In one aspect, the TiN coating 400c is disposed over the stainless steel layer 317 and the CrN coating 400a is disposed over the outer surface 311a of the assembled sealing plate 312 (including the TiN coating 400c), support base 319, and insulative housing 316. In another aspect, the TiN coating 400c is disposed over the outer surface 311a of the assembled sealing plate 312, support base 319, and insulative housing 316 and the CrN coating 400a is disposed over a portion of, or all of, the TiN coating 400c. Additionally, an HMDSO plasma coating 400b is disposed over the CrN coating 400a. As described above, in embodiments it may be useful to coat only a partial outer surface 311a of the jaw member 310 or include thicker layers of the TiN coating 400c, CrN coating 400a, and/or the HMDSO plasma coating 400b on different portions of the outer surface 311a of the jaw member 310.

Additionally, or alternatively, in embodiments, the sealing plates 312 may be coated in the manner described above with respect to FIG. 8A and the outer surface 311a of the jaw member 310 may also be coated with the TiN coating 400c, CrN coating 400a, and/or the HMDSO plasma coating 400b.

Figure 9:
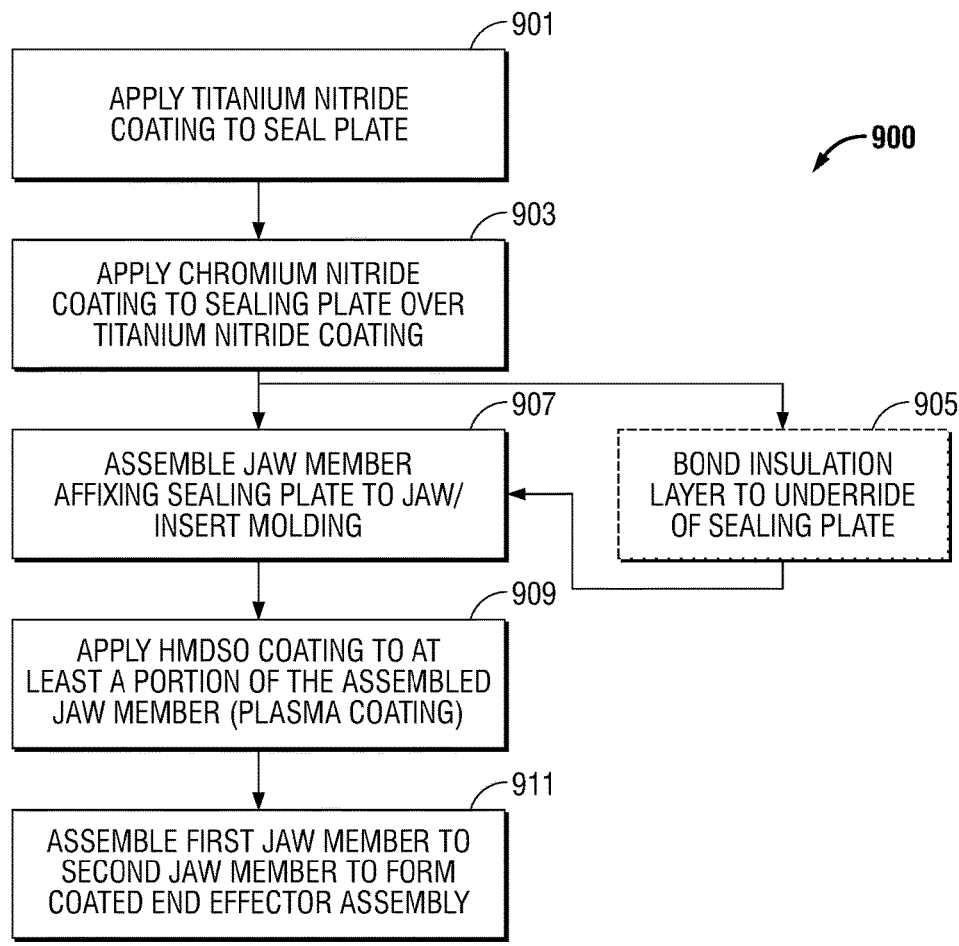
FIG. 9 is a flow chart illustrating a method of manufacturing an end effector assembly for use with an electrosurgical instrument according to an aspect of the present disclosure.

Turning now to FIG. 9, a method for manufacturing an HMDSO plasma coated end effector assembly is illustrated and will be described as method 900. Method 900 begins in step 901 where a TiN coating is applied to a sealing plate (for example, a stainless steel layer). Subsequent to coating the sealing plate with TiN (step 901), in step 903 a CrN coating and/or an HMDSO plasma coating is applied to a sealing plate over the TiN coating. Step 903 may include coating the entire TiN layer with CrN, or coating only a portion of the TiN layer with CrN. Additionally, step 903 may include depositing a CrN coating over portions of the sealing plate that have not been coated with TiN.

Method 900 may optionally also include step 905 where an insulative layer is bonded or otherwise affixed to an underside of the sealing plate. In some aspects, the insulative layer may be bonded to an entire sheet of stainless steel and the sealing plate is stamped from the sheet of stainless steel after the insulative layer is bonded to the sheet of stainless steel.

In step 907, the jaw member is assembled. Specifically, in step 907 the coated sealing plate is affixed to a support base and/or an insulative housing. In 907, the jaw member may be assembled via any suitable process including insert molding. In step 909, an HMDSO plasma coating is applied to at least a portion of the assembled jaw member. Step 909 may be carried out via plasma coating in accordance with the methods described above. The HMDSO plasma coating may be enhanced by the addition of oxygen or fluorine in the plasma and deposition. Any or all of steps 901-909, described above, are repeated to assemble an opposing (second) jaw member. In step 911, the first assembled jaw member and the second assembled jaw member are assembled to form a coated end effector assembly. That is, the first assembled jaw member is pivotably coupled to the second assembled jaw member to create the assembled coated end effector assembly.

Figure 10:
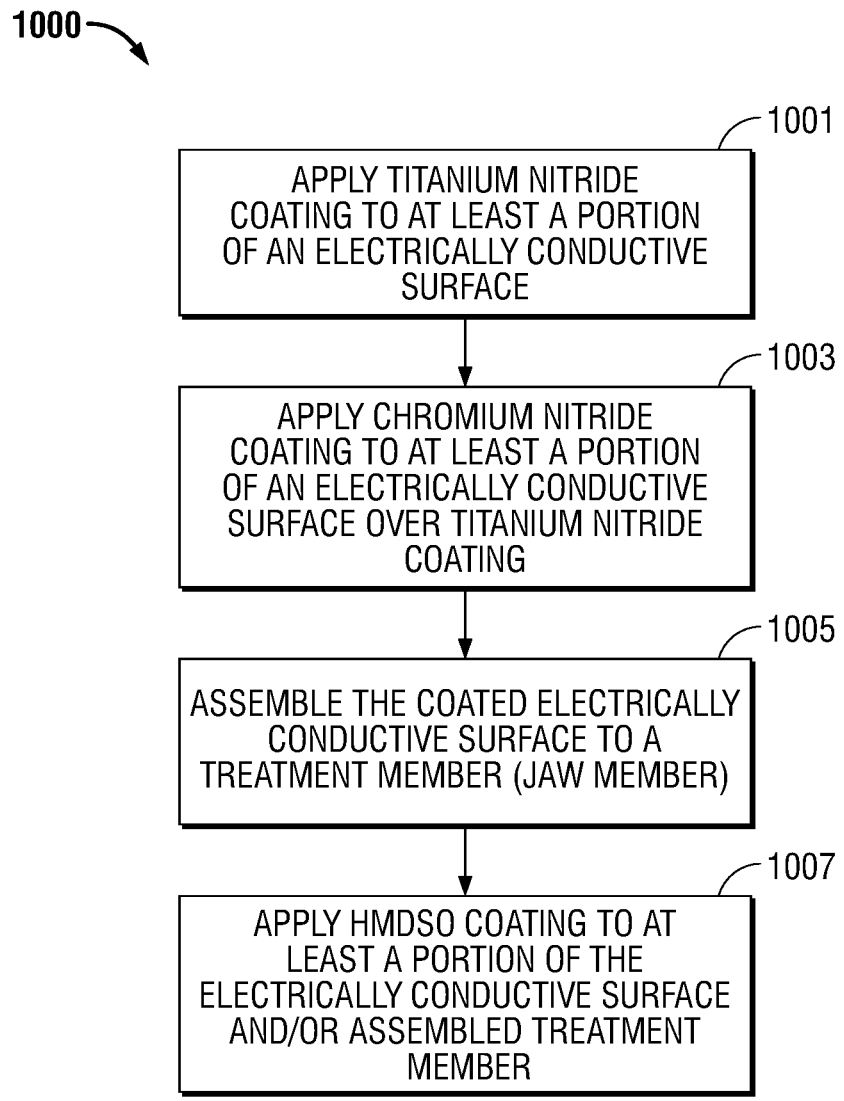
FIG. 10 is a flow chart illustrating a method of manufacturing an electrosurgical instrument according to an aspect of the present disclosure.

Turning now to FIG. 10, a method for manufacturing an HMDSO plasma coated end instrument is illustrated and will be described as method 1000. Method 1000 begins in step 1001 where a TiN coating is applied to at least a portion of an electrically conductive surface. The electrically conductive surface may be a sealing plate which may be formed of stainless steel. The stainless steel may be stamped from a large stainless steel sheet which has already been coated with any of the coatings described herein. Method 1000 may optionally also include a step where an insulative layer is bonded or otherwise affixed to an underside of the electrically conductive surface. In some aspects, the insulative layer may be bonded to an entire sheet of stainless steel and the electrically conductive surface is stamped from the sheet of stainless steel after the insulative layer is bonded to the sheet of stainless steel.

In step 1003, a CrN coating is applied over the TiN coating. As described above, step 1003 may include applying the CrN coating over portions of the electrically conductive surface that are not coated with the TiN coating. Alternatively, step 1003 may include applying the CrN coating over the entire TiN coating.

In step 1005, a treatment member is assembled. The treatment member may be a jaw member as previously described herein. Specifically, in step 1005 the coated electrically conductive surface is affixed to a support base and/or an insulative housing. In 1005, the treatment member may be assembled via any suitable process including insert molding. In step 1007, an HMDSO plasma coating is applied to at least a portion of the electrically conductive surface and/or the assembled treatment member. Step 1007 may be carried out via plasma coating the electrically conductive surface and/or the assembled treatment member. The HMDSO plasma coating may be enhanced by the addition of oxygen or fluorine in the plasma and deposition. Any or all of steps 1001-1007, described above, may be repeated to assemble the opposing (second) treatment member.

Although the above-described aspects are directed to CrN, TiN, and HMDSO coatings, it is appreciated that any nitride physical vapor deposition coating may be utilized in place of the CrN coating and/or the TiN coating. For example, other coatings that may be used in place of the CrN coating and/or the TiN coating may include TiAlCN, TiZrN, CrAlN, CrAlCN, AlCrN, multilayer designs, nanolayered coatings, nanocomposite coatings, diamond-like coatings, or any combinations thereof. Additionally, although FIGS. 8A, 8B, 9, and 10 are described as including a CrN coating over a TiN coating, it is appreciated that the TiN coating may be replaced with a CrN coating or any other coating.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawings are presented only to demonstrate certain examples of the disclosure. Other elements, steps, methods and techniques that are insubstantially different from those described above and/or in the appended claims are also intended to be within the scope of the disclosure.

What is claimed is:

1. An electrosurgical instrument, comprising:
    a handle having a shaft that extends therefrom;
    an end effector disposed at a distal end of the shaft, the end effector including:
        a support base; and
        at least one electrode assembled to the support base and adapted to couple to a source of electrosurgical energy;
    a titanium nitride coating covering at least a portion of the electrode;
    a chromium nitride coating covering at least a portion of the electrode; and
    a hexamethyldisiloxane plasma coating covering an entirety of an outer surface of the end effector including an outer surface of the support base and the at least one electrode including at least a portion of the chromium nitride coating.

2. The electrosurgical instrument according to claim 1, wherein the end effector includes a pair of opposing jaw members, at least one of the jaw members including an electrical jaw lead, the electrode coupled to the electrical jaw lead and the support base.

3. The electrosurgical instrument according to claim 1, wherein the electrode includes a stainless steel layer and wherein a hexamethyldisiloxane plasma coating is disposed over at least a portion of the stainless steel layer.

4. The electrosurgical instrument according to claim 3, further comprising an electrically insulative layer disposed on at least a portion of an underside of the stainless steel layer.

5. The electrosurgical instrument according to claim 4, wherein the electrically insulative layer is formed from a material selected from the group consisting of a polyimide, polycarbonate, and polyethylene.

6. The electrosurgical instrument according to claim 1, wherein the chromium nitride coating is disposed over at least a portion of the titanium nitride coating.

7. An end effector assembly including a pair of opposing jaw members, each of the jaw members comprising:
    a support base;
    an electrical jaw lead;
    a sealing plate coupled to the electrical jaw lead and the support base, the sealing plate having a stainless steel layer;
    a titanium nitride coating disposed over at least a portion of the stainless steel layer;
    a chromium nitride coating disposed over at least a portion of the stainless steel layer; and
    a hexamethyldisiloxane plasma coating disposed over an entirety of an outer surface of the jaw member including an outer surface of the support base and the sealing plate including the chromium nitride coating.

8. The end effector assembly according to claim 7, further comprising an electrically insulative layer disposed on at least a portion of an underside of the stainless steel layer.

9. The end effector assembly according to claim 8, wherein the electrically insulative layer is formed from a material selected from the group consisting of a polyimide, polycarbonate, and polyethylene.

10. The end effector assembly according to claim 7, further comprising an insulative housing disposed around the support base, wherein the hexamethyldisiloxane plasma coating is disposed on the sealing plate and the insulative housing.

11. The end effector assembly according to claim 7, wherein the chromium nitride coating is disposed over at least a portion of the titanium nitride coating.

12. A method of manufacturing an electrosurgical instrument, comprising:
   applying a titanium nitride coating to at least a portion of an electrically conductive surface;
   applying a chromium nitride coating to at least a portion of an electrically conductive surface to form a coated electrically conductive surface;
   assembling the coated electrically conductive surface to a treatment member by affixing the coated electrically conductive surface to a support base to form an assembled treatment member; and
   applying a hexamethyldisiloxane plasma coating over at least a portion of the assembled treatment member including both of the electrically conductive surface and the support base.

13. The method according to claim 12, wherein the assembling the coated electrically conductive surface to the treatment member includes:
   providing the support base to support the electrically conductive surface; and
   bonding an electrically insulative layer to an underside of the electrically conductive surface.

14. The method according to claim 13, further comprising overmolding an insulative material about the support base to secure the electrically conductive surface thereto.

15. The method according to claim 12, further comprising forming the electrically conductive surface by stamping the electrically conductive surface from a sheet of stainless steel.

16. The method according to claim 12, further comprising coupling an electrical lead to the electrically conductive surface, the electrical lead configured to connect the electrically conductive surface to an energy source.

17. The method according to claim 12, further comprising applying a chromium nitride coating over the titanium nitride coating.

* * * * *